(12) United States Patent
Severin et al.

(10) Patent No.: US 7,368,431 B2
(45) Date of Patent: May 6, 2008

(54) POLYPEPTIDE, THE CONJUGATE THEREOF WITH DOXORUBICINE AND A PHARMACEUTICAL COMPOSITION BASED THEREON

(75) Inventors: Evgeniy Sergeevich Severin, Moscow (RU); Sergey Evgenyevich Severin, Moscow (RU); Sergey Viktorovich Lutsenko, Moscow (RU); Sergey Michaylovich Kiselev, Moscow (RU); Natalya Borisovna Feldman, Tula (RU)

(73) Assignee: Zakrytoe Aktsionernoe Obschestvo "Russkie BiotechnologII", Moscow (RU)

( * ) Notice: Subject to any disclaimer, the term of this patent is extended or adjusted under 35 U.S.C. 154(b) by 805 days.

(21) Appl. No.: 10/872,827

(22) Filed: Jun. 21, 2004

(65) Prior Publication Data

US 2005/0070465 A1 Mar. 31, 2005

Related U.S. Application Data

(63) Continuation of application No. PCT/RU02/00544, filed on Dec. 20, 2002.

(30) Foreign Application Priority Data

Dec. 21, 2001 (RU) .............................. 2001134536

(51) Int. Cl.
| | |
|---|---|
| *A61K 38/08* | (2006.01) |
| *C07K 7/04* | (2006.01) |
| *C07K 1/107* | (2006.01) |
| *A61K 38/00* | (2006.01) |
| *A61K 38/02* | (2006.01) |
| *C07G 11/00* | (2006.01) |
| *C07K 2/00* | (2006.01) |

(52) U.S. Cl. ............................ 514/15; 514/2; 530/300; 530/327; 530/345; 536/16.8

(58) Field of Classification Search ..................... None
See application file for complete search history.

(56) References Cited

U.S. PATENT DOCUMENTS

| | | | |
|---|---|---|---|
| 4,863,902 A | 9/1989 | Amagase et al. | 514/12 |
| 5,087,616 A | 2/1992 | Myers et al. | 514/21 |
| 5,122,368 A | 6/1992 | Greenfield et al. | |
| 5,183,805 A | 2/1993 | Lee et al. | 514/13 |
| 5,349,066 A | 9/1994 | Kaneko et al. | 546/294 |
| 5,393,737 A | 2/1995 | Mayers et al. | 514/12 |
| 5,505,931 A | 4/1996 | Pribish | 424/1.11 |
| 5,622,929 A | 4/1997 | Wilner et al. | 514/8 |
| 5,776,458 A | 7/1998 | Angelucci et al. | 424/178.1 |
| 5,824,805 A | 10/1998 | King et al. | 548/546 |
| 5,969,099 A | 10/1999 | Anderson et al. | 530/327 |

FOREIGN PATENT DOCUMENTS

| | | |
|---|---|---|
| EP | 0441218 | 8/1991 |
| RU | 2107690 | 3/1998 |
| WO | 8501284 | 3/1985 |

OTHER PUBLICATIONS

Lutsenko et al., "The Enhancement of Anticancer Activity of Doxorubicin by its Targeted Delivery to Cancer Cells via Protein Vectors", Russian Oncological Journal, No. 3, pp. 33-37, 2001.

*Primary Examiner*—Andrew D. Kosar
(74) *Attorney, Agent, or Firm*—Davidson, Davidson & Kappel, LLC

(57) ABSTRACT

The inventive polypeptide is embodied in the form of a similar fragment of the epidermal growth factor of aminoacid ranging from 21 to 31 and capable of efficiently binding with the receptor of the epidermal growth factor as a vector for the directed supply of anticancer agent to tumour cells. The inventive conjugate of said polypeptide contains doxorubicine and has a selective action on cancer tumours and can substantially reduce the resistance of tumour cells with respect to the anticancer agents, the conjugated parts of said agents being binded with the aid of a chemical bond which is unstable in relation to acid hydrolysis. The inventive pharmaceutical composition comprises an efficient quantity of conjugate and a carrier which is fit for intravenous injection. Said invention can be used for medicine for treating cancer patients.

4 Claims, 2 Drawing Sheets

POLYPEPTIDE, THE CONJUGATE THEREOF WITH DOXORUBICINE AND A PHARMACEUTICAL COMPOSITION BASED THEREON

This application is a Continuation international application of PCT/RU02/00544, filed 20 Dec. 2002.

FIELD OF ENGINEERING

The invention is related to the chemistry of natural compounds, pharmacology and medicine and can be used in medicine for the treatment of cancer patients.

TECHNICAL ANCESTORS

The primary and acquired resistance of cancer cells to and low selectivity of anticancer drugs are among major factors which limit the efficacy of anticancer chemotherapy. Selectivity of these drugs can be increased via their targeted delivery directly to cancer cells by using various protein vectors as carrier. In this case, drugs penetrate in the targeted cells through a mechanism of receptor-mediated endocytosis of a conjugate in which a vector protein is covalently linked with a drug. Selectivity of the above conjugates is achieved through either the presence of specific receptors in the walls of cancer cells which are "recognizable" by the vector protein or antibody or due to a much higher level of receptors of the vector protein in the walls of cancer as compared to non-transformed cells. A presumed efficacy of the epidermal growth factor (EGF) as vector molecule is derived from its high stability, availability as a recombinant protein and a higher level of EGF-receptors in the walls of cancer cells as compared to healthy cells.

Numerous studies and patents are known which describe different conjugates of the EGF with doxorubicin (DR) and other anticancer drugs, methods of their manufacturing and pharmaceutical compositions on their basis [U.S. Pat. Nos. 5,824,805, 5,349,066, 5,087,616, 5,393,737, 5,505,931, 5,622,929, 5,122,368, 5,776,458 etc.].

Doxorubicin is a known anticancer antibiotic drug which, although widely used in clinical practice, has a number of practical drawbacks such as high cardiotoxicity and induction of quick development of resistance of cancer cells following repeated intravenous injections of the drug. The use of DR in a conjugated form could result in a considerable improvement of its therapeutic qualities.

Short-chain EGF peptide fragments are of particular interest as vector molecules to be used for the targeted delivery of DR and other anticancer drugs to cancer cells. As the method of their manufacture is relatively simple, economical and does not require using any starting materials of biological origin, conjugates derived from them are easier to standardize.

Mixtures (pharmaceutical compositions) of DR (and other anticancer drugs) with different EGF peptide fragments are known to be used in the chemotherapy of cancer [U.S. Pat. No. 4,863,902]. The authors explain an enhanced anticancer efficacy of the patented drugs by a higher sensitivity of cancer cells to DR which is due to a proliferative effect produced by the EGF and its active fragments. However, as the link between DR and EGF and its fragments in the conjugate is not covalent, the targeted delivery of the drug to cancer cells cannot be ensured, leading to an increase of the drug nonspecific toxicity.

Also known to be used in the treatment of cancer is a biological active cyclic polypeptide having an amino acid sequence similar to that of an EGF fragment from 32 to 48 amino acid [U.S. Pat. No. 5,183,805]. The patent says that the peptide fragment can be conjugated with chemical agents such as DR, but neither conjugates nor methods of their manufacture nor their biological qualities are claimed in the patent.

Also known are a polypeptide which is an EGF fragment from 21 to 31 amino acid, of the following formula:

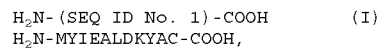

$H_2N$-(SEQ ID No. 1)-COOH        (I)
$H_2N$-MYIEALDKYAC-COOH, capable of effectively binding to EGF-receptors and causing cellular proliferation, and its conjugate with DR in which the DR-to-polypeptide ratio is 1:1 and the conjugated moieties are linked together with an acidlabile azomethine linkage as a result of using glutaric aldehyde as cross-linking agent. [*Russian Oncological Journal*, No.3, 2001, pp.33-37, The Enhancement of Anticancer Activity of Doxorubicin by its Targeted Delivery to Cancer Cells via Protein Vectors]. As pharmaceutical compositions, any compositions may be indicated, described in U.S. Pat. Nos. 5,349,066, 5,087,616, 5,122,368, which contain DR-EGF conjugates at effective concentrations and a pharmaceutical carrier suitable for intravenous administration.

DISCLOSURE OF THE INVENTION

The goal of the invention is to widen a choice of agents for the purpose described and to enhance their efficacy.

The goal is accomplished by that a new synthetic polypeptide similar to a fragment of the epidermal growth factor from 21 to 31 amino acid is proposed, which is capable of effectively binding to receptors of the epidermal growth factor, causing cellular proliferation and acting as vector for the targeted delivery of anticancer drugs to cancer cells. The polypeptide has the following formula:

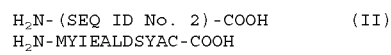

$H_2N$-(SEQ ID No. 2)-COOH        (II)
$H_2N$-MYIEALDSYAC-COOH

Unlike polypeptide (I), the proposed polypeptide has an amino acid Lys in the active center of the receptor-binding fragment of human EGF replaced with Ser which is one of the amino acids forming a binding site in murine EGF. It was established accidentally that replacement of Lys with Ser precludes undesirable conjugation at Lysine ε-amino groups in the active center of the receptor-binding fragment which, in turn, prevents the inhibition of the binding of the proposed polypetide to an EGF-receptor.

Although the efficacy of the proposed polypeptide is demonstrated in a form of a conjugate with a known antibiotic doxorubicin, other anticancer antibiotics such as vincristine, cisplatin, daunomycin, methotrexate and other anticancer agents such as toxins (such as diphtheria or ricin), cyclophosphamide and other medications, also can be used.

Also, a conjugate of the above polypeptide with doxorubicin is proposed, in which doxorubicin is covalently linked with polypeptide through an acidlabile azomethine linkage and a polypeptide MYIEALDSYAC (SEQ ID No. 2) is used as polypeptide. The conjugate acts selectively on tumors and may substantially reduce resistance of cancer cells to anticancer drugs.

Glutaric aldehyde or any other bifunctional agent can be used as cross-linking agent for linking polypeptide and doxorubicin at amino groups. As a result, a conjugate with an acidlabile linkage is obtained.

Also, a pharmaceutical composition is proposed, which shows cytotoxic activity and contains the proposed conjugate of a receptor-binding fragment of the epidermal growth factor with doxorubicin at an effective concentration (0.05-0.1%) and carriers suitable for intravenous administration.

A physiologic salt solution, phosphate saline solution or analgetic preparations can be used as carrier. The composition may additionally contain microbicidal, antiviral and antiparasitic medicines and other medications used for the treatment of cancer patients, in the amounts of no more than 50% of the total weight of the composition.

DETAILED DESCRIPTION OF THE INVENTION

Figure 1:
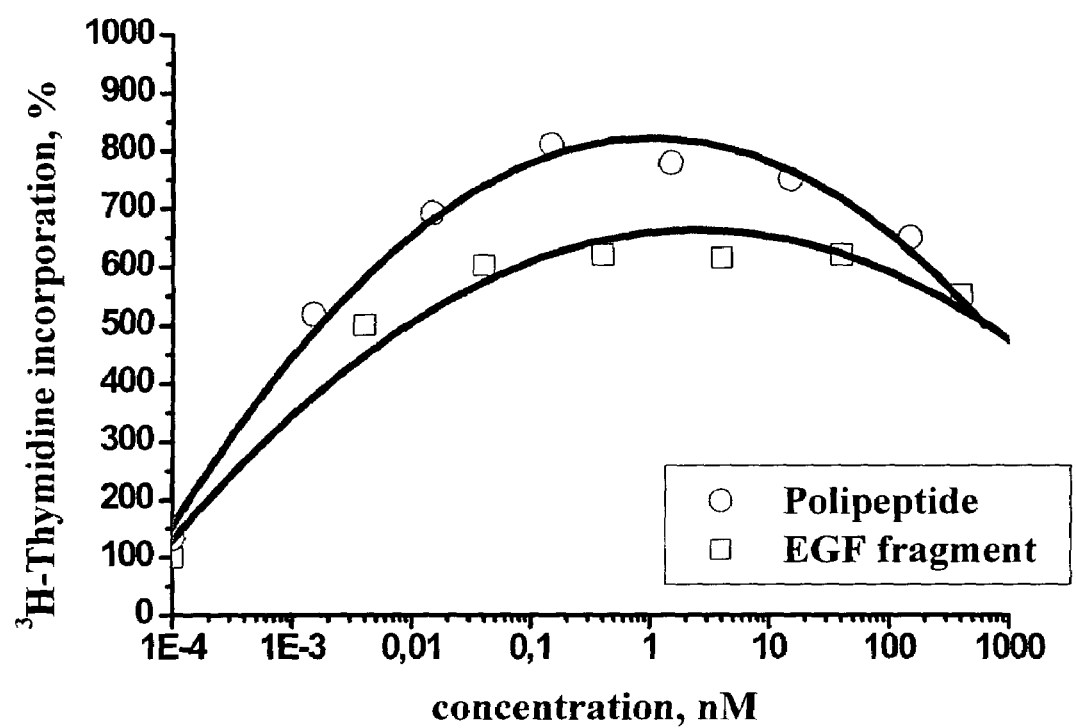
FIG. 1 presents data to compare proliferative effects of the proposed polypeptide and known polypeptide (I) on murine fibroblast cell line NIH 3T3.
X-axis: Concentration, nM
Y-axis: Incorporated $^3$H-thymidine, %
Designations: Polypeptide, EFG fragment

Below are given examples which illustrate the invention and prove the possibility of using the proposed receptor-binding fragment of the epidermal growth factor, conjugate and conjugate-based composition for the purpose described.

EXAMPLE 1

Manufacture of Polypeptide

The polypeptide was obtained by the method of solid-state peptide chemistry using a Fmoc strategy of synthesis. Wash-resin was chosen as polymer carrier. HOBt and N,N-diisopropyl carbodiimide were used to activate carboxyl groups of Fmoc-amino acids by conversion to hydroxybenzotriazolic ester at each step of peptide condensation. Fmoc-amino acids, HOBt and N,N-diisopropyl carbodiimide were taken in 10-fold molar excesses relative to amino groups of the polymer. The course of the chemical reaction was controlled by discoloration of the bromophenol blue which was added in the reactor as solution in dimethyl sulfoxide (DMSO) in the ratio 1/1000 (mol) relative to amino groups. The reaction proceeded for 1.5-2.0 hours. After the condensation was over, the resin was washed 4 times in dimethyl formamide (DMF) and then processed by a 50% solution of piperidine in DMF. The polypeptide was removed from the polymer carrier using a mixture of trifluoroacetic acid—95%, water—2.5% and 1,2-ethanedithiol—2.5%. After the resin had been filtered, the peptide was precipitated from the solution by diethyl ether. The precipitate was separated by centrifugation, dried in vacuum and analyzed by reversed-phase HPLC on a PHENOMENEX LUNA (smooth spherical silica) C18 250*3 column. Gradient elution of the polypeptide from the column was carried out with a system of the following solvents: acetonitrile-0.1% trifluoroacetic acid/water. Semipreparative reversed-phase HPLC was conducted under the same conditions on a NUCLEOSIL (high surface area spherical silica) C 18 250*8 column. The purity of the polypeptide obtained with chromatographic separations was >96%.

The obtained polypeptide was characterized by the method of mass spectrometry (molecular ion—1265). The structure of the polypeptide is given in Table 1.

TABLE 1

| Structures of the known and proposed polypeptides |
|---|
| Amino acid sequence of the prototype polypeptide (EGF fragment) (SEQ ID No. 1) |
| NH$_2$-Met-Tyr-Ile-Glu-Ala-Leu-Asp-Lys-Tyr-Ala-Cys-COOH<br>\|<br>($\epsilon$-NH$_2$) |
| Amino acid sequence of the proposed polypeptide (SEQ ID NO. 2) |
| NH$_2$-Met-Tyr-Ile-Glu-Ala-Leu-Asp-Ser-Tyr-Ala-Cys-COOH |

EXAMPLE 2

Manufacture of a Conjugate of the Polypeptide With DR

The polypeptide was dissolved in 5 ml of 0.05M phosphate buffer (pH 7) (concentration 1 mg/ml) and doxorubicin preliminary dissolved in 5 ml of distilled water (pH 5.5) (concentration 1.2 mg/ml) was added. The synthesis was run by scheme 1:

Scheme 1

POLYPEPTIDE—NH$_2$ +

$$\underset{H}{\overset{O}{\underset{\|}{C}}}-CH_2-CH_2-CH_2-\underset{H}{\overset{O}{\underset{\|}{C}}} + HN-DR =$$

= POLYPEPTIDE—N=C—CH$_2$—CH$_2$—CH$_2$—C=N—DR

Glutaric aldehyde (GA) in 0.05M phosphate buffer (pH 7.2) (concentration 0.5 mg/ml) was added drop-by-drop to the reaction mixture. The volume of the added GA was 3 ml. After that, the mixture was incubated at 50° C. for 1 hour. The obtained conjugate was separated from starting materials using a PD-10 SEPHADEX (cross-linked dextran gel) G-25 column (Pharmacia, Sweden). The conjugate was analyzed by reversed-phase HPLC on a NUCLEOSIL (high surface area spherical silica) C 18 250*4.6 column. Gradient elution of the polypeptide from the column was carried out with a system of the following solvents: acetonitrile—0.1% trifluoroacetic acid/water.

Concentration of the polypeptide in the conjugate was determined by spectrophotometry (at $\lambda$=280 nm). Concentration of DR in the conjugate was determined by spectrophotometry at $\lambda=495$ nm). The molar polypeptide-to-DR ratio in the conjugate was 1:1.

To conclude, a method is developed of chemical conjugation of the proposed polypeptide and doxorubicin with the use of glutaric aldehyde as cross-linking agent. A polypeptide-DR conjugate is obtained and characterized, in which the ratio of the conjugated moieties is 1:1.

EXAMPLE 3

Demonstration of Biological Activity of the Polypeptide

Proliferative activity of the polypeptide was tested on line NIH 3T3 murine fibroplat cells. The rate of DNA biosynthesis was judged from the amount of $^3$H-timidine incorporated in the acid-soluble cell fraction. Line NIH 3T3 murine fibroblast cells were cultivated in plastic flasks in the RPM1 medium (SIGMA), which contained 10% of fetal bovine serum (SIGMA), 100 U/mb of penicillin and 100 µg/ml of streptomycin, in a wet environment of 5% $CO_2$ at 37° C. Proliferation of synchronized line NIH 3T3 fibroblasts was induced by adding to the cellular suspension the proposed polypeptide at a different concentration (0.1-1000 ng/ml). The fibroblasts were cultivated in 96-well plates in the complete medium, 200-800 cells in each well containing 200 µl of the medium. $^3$H-thymidine (1 µCi/well, 40 µCi/mol) was added 2 hours prior to the end of the incubation period. Radioactivity was measured by a scintillation counter (RACKBETA, LKB) with the use of a toluene-based scintillation fluid ZhS-8. The rate of DNA biosynthesis was expressed as the stimulation index (stimulated-to-control cell ratio) calculated by the formula: $I=N/No\times100\%$, where I is the stimulation index, N is the number of EGF-stimulated cells, and No is the number of control cells.

FIG. 1 presents data to compare proliferative effects of the proposed polypeptide and known polypeptide I (EGF fragment) on murine fibroblast cell line NIH 3T3. The data show that the proposed polypeptide has a more pronounced dose-dependent proliferative effect on this line cells than the known polypeptide, which may be indicative of a higher affinity of the proposed polypeptide to receptors. As the expression of EGF-receptors in the walls of cancer cells is several orders of magnitude higher than that in non-transformed cells, the above finding supports a possibility of using the proposed polypeptide as a more effective vector molecule for the targeted delivery of anticancer drugs to cancer cells.

EXAMPLE 4

Efficacy of the Proposed Polypetide-DR Conjugate Against Different Cancer Cell Lines, Evaluated by the Rate of Survival Efficacy of the conjugate was studied on the following cell lines: human breast carcinoma cell line MCF-7$^{wt}$ and resistant human breast carcinoma cell line MCF-7$^{AdrR}$; human ovary carcinoma cell line SKOV3 and resistant human ovary carcinoma cell line SKVLB; and murine melanoma cell line B16.

Study protocol was common for all test runs. The cells cultivated in plastic flasks (COSTAR) in the RPMI medium (SIGMA), which contained 10% of fetal bovine serum (SIGMA), 100 U/ml of penicillin and 100 µg/ml of streptomycin, in a wet environment of 5% $CO_2$ at 37° C., were inoculated in 96-well plates (Costar), 10000 in each well, and studied drugs were then added at different concentrations. After that, the cells were incubated for 72 hours. Two-four hours prior to the end of the incubation period, 50 µl (1 mg/ml) of the MTT solution (3-[4,5-dimethylthiazole-2yl]-2,5-diphenyltetrazole bromide (SIGMA) in the culture medium were added in each well. After the development of coloration, the medium was removed, formazan crystals were dissolved in 150 µl of dimethyl sulfoxide, and the absorbance was measured by spectrophotometry at 540 nm. Survival rates of the cells exposed to free and conjugated DR were determined in percent relative to the survival rate of controls taken as 100%.

Survival rates of the cells exposed to free doxorubicin and doxorubicin conjugated with either proposed polypeptide or EGF fragment are given in Table 2.

TABLE 2

| | Survival rates of the cells exposed to free or conjugated doxorubicin | | |
|---|---|---|---|
| | Cytotoxicity ($IC_{50}$) | | |
| Cellular line | DR | EGF fragment-DR conjugate | Polypeptide-DR conjugate |
| MCF-7$^{wt}$ | 58.6 nM | 2.5 nM | 1.3 nM |
| MCF-7$^{AdrR}$ | 3.7 µM | 0.3 µM | 0.15 µM |
| SKOV3 | 209 nM | 35 nM | 22 nM |
| SKVLB$^{AdrR}$ | 2.01 µM | 0.2 µM | 0.07 µM |
| B16 | 35 nM | 1.5 nM | 1.1 nM |

It follows from the data presented that the proposed conjugate of polypeptide with doxorubicin has a much more pronounced toxic effect on human cancer cell lines MCF-7$^{wt}$ and SKOV3, which are doxorubicin-sensitive, and murine melanoma cell line B16 than free DR or its conjugate with EGF fragment (prototype). Also, the proposed conjugate of polypeptide with doxorubicin shows a high cytotoxic activity against cell lines MCF-7$^{AdrR}$ and SKVLB which are resistant to anthracycline antibiotics.

To conclude, an anticancer drug (doxorubicin) conjugated with the proposed polypeptide is shown to have a pronounced toxic effect on cancer cells, both sensitive and resistant to doxorubicin, which fact proves the efficacy of the proposed polypeptide as vector molecule for the targeted delivery of anticancer drugs in vitro.

EXAMPLE 5

Pharmaceutical compositions for injections are obtained by dissolving the conjugate in a physiological salt solution or phosphate saline solution with pH about 7.4. concentration of the conjugate in the solution is 0.05-0.1%.

EXAMPLE 6

Cytotoxic activity of a composition of the polypeptide-DR conjugate with a physiological solution (described in Example 5) demonstrated in a murine implanted tumor model.

Figure 2:
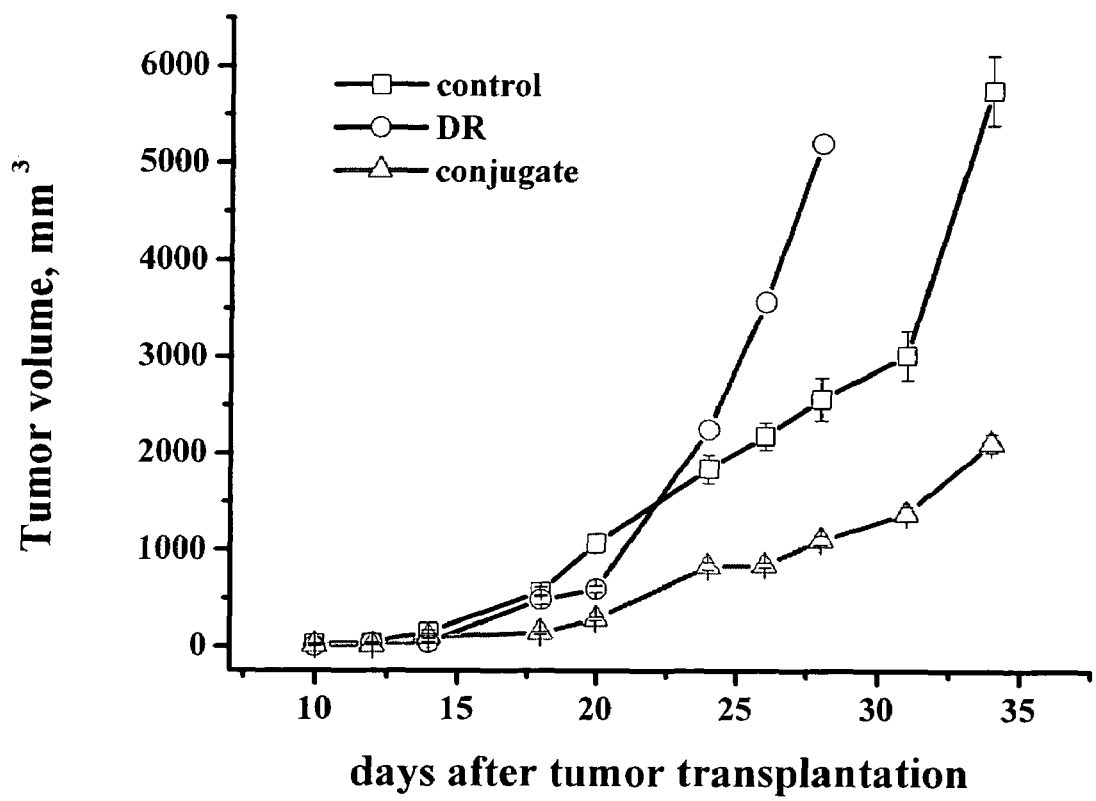
FIG. 2 presents data demonstrating a delay in the onset of tumors and their growth retardation as a result of administration of DR-containing compositions, in a murine implanted tumors model.
X-axis: Days after the cancer implantation
Y-axis: Tumor size: mm$^3$
Designations: Controls; DR; Conjugate

To demonstrate cytotoxic activity of the polypeptide-DR conjugate against solid tumors, pharmaceutical compositions described in Example 5 were administered intravenously to mice with subcutaneously implanted line B16 cancer cells. The results obtained are given in FIGS. 1 and 2. The medicines were administered at a dose of 0.2 mg/kg of doxorubicin once every four days, three injections in total, starting from day 3 after the cancer implantation.

An increase in the average duration of life and higher tumor growth inhibition rates suggest a therapeutic efficacy of the targeted delivery of an anticancer agent in the proposed composition in vivo.

A conjugate of the proposed polypeptide with an anthracycline antibiotic doxorubicin (polypeptide-DR) is shown (Examples 4, 6) to exert a therapeutic action on solid tumors when given intravenously.

```
AMINO ACID SEQUENCE OF THE PROPOSED POLYPEPTIDE
                                        (SEQ ID NO: 2)
     Met-Tyr-Ile-Glu-Ala-Leu-Asp-Ser-Tyr-Ala-Cys.
      1                   5                      10
```

---

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial
<220> FEATURE:
<223> OTHER INFORMATION: Known Polypeptide

<400> SEQUENCE: 1

Met Tyr Ile Glu Ala Leu Asp Lys Tyr Ala Cys
1               5                   10

<210> SEQ ID NO 2
<211> LENGTH: 11
<212> TYPE: PRT
<213> ORGANISM: Artificial
<220> FEATURE:
<223> OTHER INFORMATION: Modified polypeptide
<220> FEATURE:
<221> NAME/KEY: MUTAGEN
<222> LOCATION: (8)..(8)

<400> SEQUENCE: 2

Met Tyr Ile Glu Ala Leu Asp Ser Tyr Ala Cys
1               5                   10
```

---

It follows from FIG. 1 that, unlike free DR, its conjugate caused a considerable delay in the onset of tumors and slowed their growth. The tumor growth inhibition rate was 58%.

It follows from Table 3 that the proposed conjugate has a therapeutic effect when given intravenously, which could be seen from an increase in the average duration of life (ADL) of laboratory animals. Unlike free doxorubicin, administration of its conjugate allowed a 46% increase in ADL to achieve.

TABLE 3

Increase in the average duration of life of animals treated intravenously with DR-containing compositions

| Animal group | ADL, days | Increase in ADL, % |
|---|---|---|
| Controls | 31.4 ± 4.8 | — |
| DR | 23.6 ± 4.0 | −24.8 |
| Conjugate | 46.6 ± 5.7 | 48.5 |

What is claimed is:

1. A peptide consisting of SEQ ID NO: 2.
2. A peptide-doxorubicin conjugate, wherein the peptide is SEQ ID NO: 2 and the peptide and doxorubicin are covalently linked through a linker derived from glutaric aldehyde and wherein the bond between the linker and the polypeptide and the bond between the linker and doxorubicin are acid labile azomethine bonds.
3. A peptide-doxorubicin conjugate wherein the peptide is SEQ ID NO: 2, wherein said conjugate is formed by reacting SEQ ID NO: 2 with glutaric aldehyde and doxorubicin, thereby forming a covalent linkage of SEQ ID NO: 2 to doxorubicin through an azomethine linkage.
4. A pharmaceutical composition containing the peptide-doxorubicin conjugate of claim 2 or 3, and a pharmaceutically acceptable carrier suitable for intravenous administration.

* * * * *